(12) United States Patent
Brodsky et al.

(10) Patent No.: US 7,969,562 B2
(45) Date of Patent: *Jun. 28, 2011

(54) METHOD AND APPARATUS FOR MEASURING THE BIREFRINGENCE AUTOCORRELATION LENGTH IN OPTICAL FIBERS

(75) Inventors: Mikhail Brodsky, Millburn, NJ (US); Peter Magill, Freehold, NJ (US); Mikhail Boroditsky, South Amboy, NJ (US); Cristian Antonelli, Sulmona (IT); Antonio Mecozzi, L'Aquila (IT)

(73) Assignee: AT&T Intellectual Property I, L.P., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/644,911

(22) Filed: Dec. 22, 2009

(65) Prior Publication Data

US 2010/0123896 A1       May 20, 2010

Related U.S. Application Data

(63) Continuation of application No. 12/001,155, filed on Dec. 10, 2007, now Pat. No. 7,688,430.

(51) Int. Cl.
*G01N 21/00* (2006.01)
*G01J 4/00* (2006.01)
*G01N 21/41* (2006.01)

(52) U.S. Cl. .......... 356/73.1; 356/73; 356/128; 356/364

(58) Field of Classification Search .................. None
See application file for complete search history.

(56) References Cited

U.S. PATENT DOCUMENTS

| | | | | |
|---|---|---|---|---|
| 5,317,147 A | * | 5/1994 | Dandliker et al. | 250/227.17 |
| 6,204,924 B1 | * | 3/2001 | Cyr | 356/453 |
| 6,229,599 B1 | * | 5/2001 | Galtarossa | 356/73.1 |
| 6,456,370 B1 | * | 9/2002 | Ingles, Jr. | 356/73.1 |
| 6,724,469 B2 | * | 4/2004 | Leblanc | 356/73.1 |
| 7,330,245 B2 | * | 2/2008 | Froggatt | 356/73.1 |
| 7,349,077 B2 | * | 3/2008 | Caponi et al. | 356/73.1 |
| 7,373,027 B2 | * | 5/2008 | Wuilpart | 385/11 |
| 7,406,234 B2 | * | 7/2008 | Palmieri | 385/123 |
| 7,463,346 B2 | * | 12/2008 | Goto et al. | 356/73.1 |
| 7,534,055 B2 | * | 5/2009 | Debut et al. | 385/95 |
| 7,538,883 B2 | * | 5/2009 | Froggatt | 356/477 |
| 7,688,430 B2 | * | 3/2010 | Brodsky et al. | 356/73.1 |

OTHER PUBLICATIONS

Wuilpart et al., "Fully-distributed Polarization Properties of an Optical Fibre Using the Backscattering Technique," 2000, Applications of Photonic Technology 4, Roger A. Lessard, George A. Lampropoulos, Editors, Proceedings of SPIE vol. 4087, pp. 396-404.*

* cited by examiner

*Primary Examiner* — Tarifur Chowdhury
*Assistant Examiner* — Gordon J Stock, Jr.

(57) ABSTRACT

Disclosed is a method and apparatus for determining the birefringence autocorrelation length of a fiber in a non-destructive manner. The PMD of an optical fiber is measured over a first optical spectrum. A Faraday rotation angle is measured over a second optical spectrum. The birefringence autocorrelation length is determined from the measuring of the PMD and the Faraday rotation angle.

8 Claims, 3 Drawing Sheets

METHOD AND APPARATUS FOR MEASURING THE BIREFRINGENCE AUTOCORRELATION LENGTH IN OPTICAL FIBERS

This application is a continuation of prior application Ser. No. 12/001,155 filed Dec. 10, 2007, which is incorporated herein by reference.

BACKGROUND OF THE INVENTION

The present invention relates generally to optical fibers, and more particularly to measuring the birefringence autocorrelation length in optical fibers.

Fiber optic technology and fiber optic transmission systems have revolutionized telecommunications. The main driving force behind this revolution is the promise of extremely high communications bandwidth. A single wavelength of modulated laser light can carry vast amounts of information sufficient to comprise literally hundreds of thousands of phone calls or hundreds of video channels.

In a fiber optic transmission system, information may be conveyed on multiple optical signals, each centered on a different wavelength. Digital signals can be represented by modulating laser light, e.g., by rapidly turning the laser light on and off to represent the two possible states of a digital bit, i.e., "1" and "0", or "on" and "off". This process may be referred to as on-off-keyed modulation. Other types of modulation of the light also exist to convey information, including both digital and analog forms. The wavelength signal is generally emitted from a device called an optical transmitter such as a laser. In the frequency domain, this signal is centered about a frequency of the optical carrier, such as, for example, 193,000 GHz, but the signal may also include numerous frequency components spaced very closely about the nominal center frequency.

An optical signal is transmitted in a fiber optic transmission system using, generally, an optical transmitter, which includes a light source or laser, an optical fiber, optionally optical amplifier(s), and an optical receiver. A modulated optical signal arriving at an optical receiver must be of sufficient quality to allow the receiver to clearly distinguish the modulation pattern of the light sent by the transmitter (e.g., the on- and off-pulses). Noise, attenuation, and dispersion are a few of the impairments that can distort an optical signal and render the optical) signal marginal or unusable at the receiver. The distortion of an optical signal makes it extremely difficult or impossible for an optical receiver to accurately detect and reconstitute the original signal. Some of these distortions broaden the various light pulses, potentially resulting in overlapping pulses so that it is difficult to distinguish the various pulses from each other. This may result in increased errors in transmitting information. Conventionally, a properly designed optical link can maintain a sufficiently low Bit Error Rate ("BER").

Dispersion can be a major contributor to the distortion of an optical signal, which may increase the BER of the optical signal. The distortion caused by dispersion generally increases as the bandwidth of each light pulse or data rate increases and as the optical fiber transmission distance increases.

One type of dispersion is Polarization Mode Dispersion ("PMD") which is an effect related to the polarization of the optical signal. It is well known that monochromatic light (as from a laser) is polarized and that, for a given beam of light, the state of this polarization may be expressed with excellent approximation in terms of two principal polarization modes represented by two orthogonal axes that are normal to the axis of propagation. Thus, an optical signal may be considered as a superposition of two polarization signals, each aligned with the two principal polarization modes of the fiber. As such an optical signal propagates through the optical fiber, the two polarization signals travel or propagate at different speeds, due to the birefringence (or double refraction) of that fiber. The different velocities associated with the two different principal polarization modes result in one of the two polarization signals leading the other polarization signal. The delay between the leading signal and the trailing signal is referred to as the Differential Group Delay ("DGD") (denoted by $\tau$). This speed difference in the two polarization signals causes pulse broadening and restricts the usable bandwidth of each optical carrier.

At each frequency, two polarization axes may be identified in a fiber—a fast axis and a slow axis. Light that is polarized along the fast axis has a greater velocity than light which is polarized along the slow axis. Light polarized along either of these axes is said to be in a principal polarization state. Any signal propagating in that fiber can be expressed as a combination of signals polarized along these two axes—i.e. as a combination of the two principal polarization states. The "polarization state" of the light expresses how much of the light is polarized along each of the axes as well as the relative phase between these two components. The light in a pulse is usually a mixture of both polarizations and will therefore spread due to the velocity difference between the portion of the light polarized along the fast and slow axes. This velocity difference is due to the birefringence of the fiber, a characteristic or property of the material. And just as the state of polarization can be thought of as having a specific orientation, so too the local birefringence has an orientation with respect to the fiber.

In many optical fibers, not only is birefringence present, but the birefringence is nonuniform and varies along the length of the fiber. In other words, the local birefringence, $\beta(z)$, as a function of the position z along the fiber, may vary in either magnitude or orientation.

Many different phenomena may contribute to causing the birefringence, including, for example, asymmetrical fiber optic transmission media, mechanical stresses and strains applied to the fiber optic media, and other physical phenomena such as temperature gradients and changes. With these multiple phenomena affecting the birefringence in an essentially random fashion along a fiber, $\beta$ becomes a statistical quantity. Depending on the number and magnitude of these sundry causes, $\beta(z)$ may vary slowly or rapidly along the fiber. Beginning at an arbitrary point z=0 in the fiber, typically there is a small distance over which $\beta(z)$ changes very little, and then there will be a distance over which it is changing, becoming less correlated with the magnitude and orientation of $\beta(0)$. Following that, $\beta(z)$ will become completely decorrelated with $\beta(0)$. Thus, a calculation of the normalized autocorrelation of $\beta$ for a given fiber will have a specific width (e.g., when the autocorrelation falls from 1 to ½) which corresponds to the distance along the fiber for which the local birefringence changes only slightly in orientation or magnitude. This quantity is commonly referred to as the birefringence autocorrelation length.

A fiber traditionally has to be cut in order to measure the local birefringence $\beta(z)$ or its autocorrelation length. This destructive procedure is necessary because the birefringence varies along the fiber's length and spatially-resolved polarization-sensitive optical techniques (such as polarization optical time-domain reflectometry, P-OTDR) cannot determine all types of birefringence. Specifically, P-OTDR is incapable of sensing any local circular birefringence in the fiber because the probe light must retrace its path through the exact same local birefringence, but in the reverse direction.

In order to determine the birefringence autocorrelation length in a fiber, the fiber is cut into particular sections, and the DGD, for example, is determined for each fiber section. The fiber's DGD is then plotted against the fiber's length to determine the relationship between the fiber's DGD and its length. It has been found that when local birefringence is constant in orientation and magnitude, the DGD associated with the fiber is a linear function of the fiber's length. When β varies significantly over length, the relationship between a fiber's DGD and its length is proportional to $\sqrt{L}$. The crossover point between a linear relationship of DGD with length and a $\sqrt{L}$ relationship is often viewed as representing the birefringence autocorrelation length.

The birefringence autocorrelation length is often viewed as being extremely important in describing the polarization properties of a fiber and so there is great interest in measuring a fiber's birefringence autocorrelation length. However, as discussed, the use of destructive techniques to measure this value introduces a new set of problems. For example, connecting the many segments of a fiber after cutting it to determine the birefringence autocorrelation length may introduce abnormalities and deformities (such as additional loss and reflections). But, even with optically perfect splices, such a procedure is very labor intensive and therefore costly.

As a result, there remains a need to determine the birefringence autocorrelation length of a fiber in a non-destructive manner.)

BRIEF SUMMARY OF THE INVENTION

In accordance with an embodiment of the present invention, the birefringence autocorrelation length of a fiber is determined in a non-destructive manner. The PMD of an optical fiber is measured at many frequencies over a first optical spectrum. A Faraday rotation angle is measured at multiple frequencies over a second optical spectrum for a given magnetic field strength along the direction of the propagation of the light. The birefringence autocorrelation length is determined from the measurements of the PMD and the Faraday rotation angle. C1

In one embodiment, a beat length is determined from the measurement of the PMD and the Faraday rotation angle. Further, a birefringence autocorrelation length is determined from the measuring of the PMD and the Faraday rotation angle. In one embodiment, the birefringence is linear. A representation of the birefringence may lie on the equator of a Poincaré sphere. In one embodiment, a derivative of the birefringence is determined. The derivative may lie on the equator also. The birefringence autocorrelation length, $L_F$, from the equation $$\langle \tau^2 \rangle \langle \theta_F^2 \rangle = \frac{16 \beta_F^2 L^2}{\omega_{62}} \left[ 1 + \left( \frac{4\pi L_F}{L_t} \right)^2 \right]$$

can then be determined.

These and other advantages of the invention will be apparent to those of ordinary skill in the art by reference to the following detailed description and the accompanying drawings.

DETAILED DESCRIPTION

Figure 1:
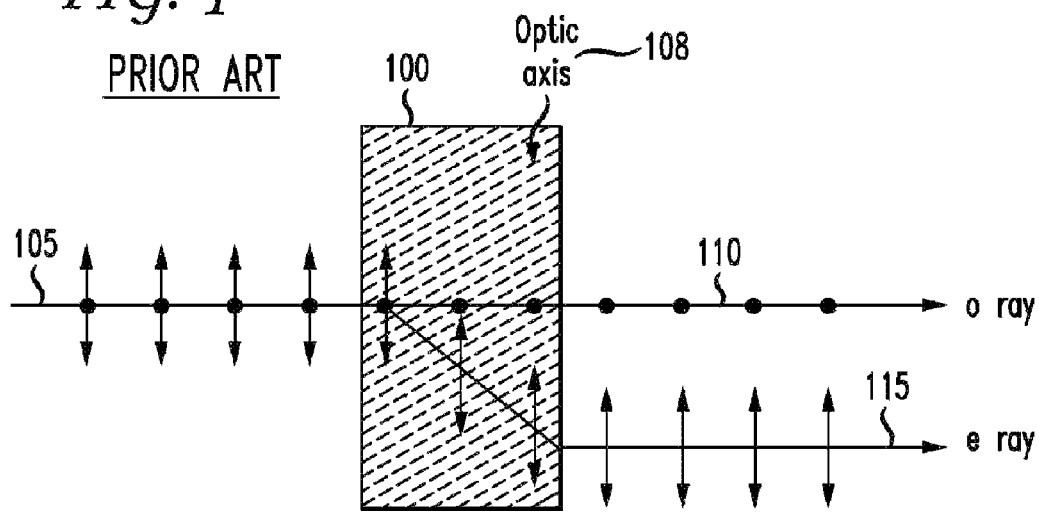
FIG. 1 is a prior art block diagram of a material (e.g., crystal) exhibiting birefringence.

As described above, birefringence is a property or characteristic of a fiber. Inside the fiber, there are two axes—a slow axis and a fast axis. When two pulses are sent along the fiber, each pulse may travel along the fiber at different speeds. As a result, the pulses have a differential group delay (DGD) (typically measured in picoseconds) from polarization mode dispersion (PMD). In accordance with an embodiment of the present invention, the PMD of a fiber is determined. The PMD of a fiber may be determined using well-known techniques or devices that measure the PMD of a fiber. The PMD is measured over a range of optical frequencies in order to determine an average PMD for the fiber. In one embodiment, the range of frequencies at which PMD is measured is 1500 nm to 1600 nm.

Further, in accordance with an embodiment of the present invention, a Faraday rotation angle for the fiber is measured. The Faraday rotation angle (typically measured in radians) is measured by applying a magnetic field to the fiber over a range of optical frequencies. This range of optical frequencies may be the same as or different than the range of optical frequencies used to) measure the PMD of the fiber. In accordance with an embodiment of the invention, the Faraday effect is not masked by the birefringence of the fiber.

The autocorrelation length of the fiber is then determined from the PMD of the fiber and the Faraday rotation angle of the fiber. As a result, instead of having to cut a fiber to determine the autocorrelation length of the fiber, an embodiment of the present invention enables the determination of the autocorrelation length of the fiber without having to destroy a fiber or a section of a fiber.

1. Fiber Birefringence, Beat Length, and Birefringence Autocorrelation Length

As described above, birefringence, or double refraction, is a complex phenomenon that occurs in materials (such as calcite and other noncubic crystals and in some stressed plastics such as cellophane). In most materials, the speed of light is the same in all directions. These materials are known as isotropic. Because of their atomic structure, birefringent materials are anisotropic. Anisotropic means that the speed of light depends on its direction of propagation through the material. When a light ray is incident on such materials, the light ray may be separated into two rays called the ordinary ray and the extraordinary ray. These rays are polarized in mutually perpendicular directions, and they travel with different speeds. Depending on the relative orientation of the material and the incident light, the rays may also travel in different directions.

There is one particular direction in a birefringent material in which both rays propagate with the same speed. This direction is called the optic axis of the material. The optic axis is actually a direction rather than a line in the material. Nothing unusual happens when light travels along the optic axis. When light is incident at an angle to the optic axis, however, the rays travel in different directions and emerge separated in space.

FIG. 1 is a typical block diagram of a material (e.g., crystal) 100 exhibiting birefringence. A narrow beam of light 105 incident on material 100 (at an angle relative to optic axis 108) is split into two beams—ordinary ray (o ray) 110 and extraordinary ray (e ray) 115. The o ray 110 and e ray 115 have perpendicular polarizations. If the material 100 is rotated, the extraordinary ray 115 rotates in space.

If light is incident on a birefringent plate perpendicular to its crystal face and perpendicular to the optic axis, the two rays travel in the same direction but at different speeds. The number of wavelengths in the two rays in the plate is different because the wavelengths of the rays differ. The rays emerge with a phase difference that depends on the thickness of the plate and on the wavelength of the incident light.

If the material has a single optic axis, or axis of anisotropy (i.e., it is uniaxial), birefringence can be formalized by assigning two different refractive indices to the material for different polarizations. The birefringence magnitude is then defined by:

$$\Delta n = n_e - n_o$$

where $n_o$ and $n_e$ are the refractive indices for polarizations perpendicular (ordinary) and parallel (extraordinary) to the optic axis.

Formally, birefringence is described by a birefringence vector $\vec{\beta}(z)$ in Stokes space, whose orientation coincides with the orientation of the slow eigenstate and whose magnitude is given by $$\beta(z) = (n_1 - n_2)\frac{\omega}{c},$$

with $n_1$ and $n_2$ being the local, frequency dependent, refractive indices corresponding to the slow and fast eigenstates, respectively and with c denoting the velocity of light in vacuum.

The strength of the birefringence (i.e. the magnitude of the birefringence vector), can be equivalently represented in terms of the so-called beat length $$L_B = \frac{2\pi}{\beta},$$

which is the length of a uniformly birefringent fiber needed for the propagating signal to return to its original state of polarization. In most fibers, the birefringence vector, and consequently also the beat length, change randomly along the propagation axis, thereby creating a host of complicated phenomena. The average beat length $<L_B>$ is often used as one of the fiber specification parameters. This averaged quantity is not an inverse of the average Birefringence $$<L_B> \neq \frac{2\pi}{<\beta>},$$

but rather the average of the inverse birefringence $$<L_B> = \left\langle \frac{2\pi}{\beta} \right\rangle,$$

which are not the same.

The autocorrelation of the random function $\vec{\beta}(z)$ has a certain characteristic width $L_0$, which is (as described above) called the birefringence autocorrelation length. Fiber birefringence $\vec{\beta}(z)$ is typically a continuous smooth function of distance z. It can, however, be assumed that the strength of the birefringence $\vec{\beta}(z)$ does not typically change much over a section of fiber whose length is shorter than $L_0$. Thus a long fiber is often thought of as a concatenation of a large number (N) of sections, each of a specific finite length $L_i$. The length $L_i$ varies randomly around its average value, equal to the birefringence autocorrelation: $L_0 = \langle L_i \rangle$. In this representation, referred to as the "birefringence waveplate model", each section i has a constant value of birefringence $\beta_i$, which varies among the sections both in magnitude and direction. The value of $L_0$ is typically important in describing polarization properties of a fiber, however, at this moment no reliable procedure exists that can measure the fiber birefringence autocorrelation length directly. Indirect methods utilized by fiber manufactures indicate that for modern fibers, $L_0$ is about tens of meters long.

The birefringence autocorrelation length $L_0$ is typically not the length used for PMD modeling purposes. Customarily, the fiber birefringence $\beta(z)$ is expanded to the first order in frequency:

$$\vec{\beta}(z) = \vec{\beta}_0 + \vec{\beta}_1(\omega)\delta\omega, \qquad (1)$$

where $$\vec{\beta}_1(\omega, z) = \frac{\partial \vec{\beta}(\omega, z)}{\partial \omega},$$

and the frequency independent term $\vec{\beta}_0(z)$ is called the birefringence at the center frequency. PMD calculations are usually made in a reference frame of the central frequency, which rotates along the fiber's length following its $\vec{\beta}_0(z)$ profile. As a result, the first term $\vec{\beta}_0(z)$ does not enter the PMD calculations, and each of the fiber sections has its PMD vector equal to $$\vec{\tau}_i = \frac{\partial}{\partial \omega}(\vec{\beta}_i L_i) = \vec{\beta}_{1i} L_i.$$

In this case, section lengths are defined based on the width $L_1$, which is the autocorrelation length of the derivative of the birefringence with frequency $\vec{\beta}_1(z)$. In one embodiment, the scales $L_0$ and $L_1$ are treated as the same.

2. Magnitude of a PMD Vector and Faraday Rotation Angle for one Fiber Section, the Same for Many Concatenated Sections One section (an $i^{th}$ section) of a fiber has a birefringence strength $$\beta_i = \frac{\omega}{c} \Delta n$$

and can be ascribed a PMD vector $\vec{\tau}_i$, whose magnitude is given by:

$$\tau_i = \frac{\partial \beta_i}{\partial \omega} \approx \frac{\Delta n + \omega \frac{\partial (\Delta n)}{\partial \omega}}{c} L_i \approx \frac{\Delta n}{c} L_i, \quad (2)$$

where quantity $\Delta n$ is generally unknown, although it is usually assumed to depend weakly on the frequency. An external magnetic field of strength B, when applied along the fiber axis of the same section, causes additional circular birefringence in the section $\beta_i^F$—a phenomenon called the Faraday Effect. One consequence of the Faraday Effect acting alone is polarization rotation of the incident polarized light beam by an angle $\theta_i$. Conventionally, the strength of the Faraday Effect is described through the magnitude of $\theta_i$ and is given by:

$$\theta_i = V \frac{B[T]}{\mu_0} L_i, \quad (3)$$

where V is an empirical constant called the Verdet constant of the fiber (V=0.75×10$^{-6}$ rad/Ampere for λ=1550nm in optical fibers), B is the strength of magnetic field measured in Tesla, and $$\mu_0 = 4\pi \times 10^{-7} \frac{\text{Tesla} \times \text{meter}}{\text{Ampere}}.$$

The magnetic) field-induced birefringence is $$\beta_i^F = 2 \times V \frac{B[T]}{\mu_0},$$

which is equal to 6×10$^{-5}$ rad/m for B=50μT (the approximate strength of the geomagnetic field).

For a fiber of total length L consisting of a large number (N) of identical concatenated sections, each of length $L_i$ and birefringence $\beta_i$, the frequency average of the total PMD vector magnitude $\tau_\Sigma$ could be related to that of an individual section:

$$\tau_\Sigma \approx \sqrt{N} \tau_i \approx \sqrt{\frac{L}{L_i}} \tau_i \approx \sqrt{LL_i} \frac{\Delta n}{c} \quad (4)$$

Figure 2:
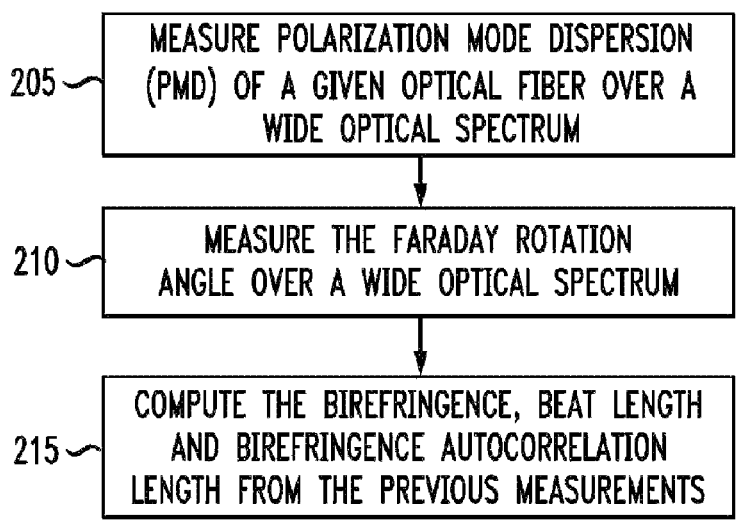
FIG. 2 is a flowchart illustrating the steps performed by a computer to determine the polarization birefringence, the beat length, and the birefringence autocorrelation length of a fiber in accordance with an embodiment of the present invention.

3. Method for Measuring the Polarization Birefringence, the Beat Length, and the Birefringence Autocorrelation Length of a Fiber FIG. 2 is a flowchart illustrating the steps performed by a computer to determine the polarization birefringence, the beat length, and the birefringence autocorrelation length of a fiber. The PMD of a given optical fiber is measured over a wide optical spectrum (i.e., for multiple wavelengths) in step 205. In step 210, the Faraday rotation angle of the fiber is measured over a wide optical spectrum (i.e., for multiple wavelengths). Some or all of the wavelengths used during the measurement made in step 210 may be the same as or different than some or all of the wavelengths used during the measurement made in step 205. In step 215, the birefringence, beat length, and/or birefringence autocorrelation length is then computed from the previous measurements (i.e., from the measurements of the PMD and the Faraday rotation angle. Thus, these fiber characteristics can now be measured in a non-destructive and reliable manner.

4. Theory of the Faraday Effect in a Linear Birefringence Compensated Long Fiber Link Let the birefringence of a long fiber be represented by the Stokes vectors $\vec{\beta}_0(z)$. The birefringence caused by the Faraday effect under the influence of the geomagnetic field can be represented by $\vec{\beta}_F(z)$. Consider a round-trip configuration with a Faraday mirror at the end of a fiber span of length L. A Faraday mirror is a device which reverses the direction of propagation while rotating by 180 degrees the state of polarization in the Stokes space. Conventional metallic or glass mirrors do not exhibit this capability. Using a folded longitudinal coordinate, with z going from 0 to 2L, in the forward propagation, the longitudinal coordinate is $0 \leq z \leq L$, whereas in the backward propagation the z is reversed with $L < z \leq 2L$. Apart from an inversion of the Stokes vector of the field, and the inversion of the z axis that makes the backward reference frame left-handed if the forward was right-handed, the reflection by the Faraday mirror produces, in the second half, an equivalent linear birefringence $\vec{\beta}_0(2L-z) = -\vec{\beta}_0(z)$. The polarization evolution in the backward propagation consequently undoes the effect of the forward propagation. On the contrary, the non-reciprocity of the Faraday effect gives $\vec{\beta}_F(2L-z) = \vec{\beta}_F(z)$. The evolution equation for the forward and backward propagation is such that $$\frac{d\hat{s}}{dz} = [\vec{\beta}_0(z) + \vec{\beta}_F(z)] \times \hat{s}, \quad (5)$$

where $\hat{s}$ is the state of polarization (SOP) vector. The explicit dependence on the linear birefringence in the above equation may be eliminated by establishing a reference frame that rotates with the linear birefringence, where $\tilde{s}(z) = R(z)\hat{s}(z)$ and $\tilde{\beta}_F(z) = R(z)\vec{\beta}_F(z)$, such that $$\frac{dR}{dz} + R[\vec{\beta}_0(z) \times] = 0. \quad (6)$$

The evolution equation of the SOP in the rotated reference frame simplifies to $$\frac{d\tilde{s}}{dz} = \tilde{\beta}_F(z) \times \tilde{s}. \quad (7)$$

The formal solution of (7), after one round-trip, is a rotation of the input SOP, that can be described by means of the rotation vector $\vec{\theta}_F$, such that $\hat{s}(2L) = \exp(\vec{\theta}_F \times)\hat{s}(0)$. Given the weak ness of the Faraday effect caused by the earth's magnetic field, the rotation angle $\theta_F = |\vec{\theta}_F|$ is expected to be small, making the following approximation legitimate:

$$\vec{\theta}_F = \int_0^{2L} \vec{\beta}_F(z) dz. \tag{8}$$

Moreover, the equality $\vec{\beta}_0(2L-z) = -\vec{\beta}_0(z)$, along with Eq. (6) implies that $R(2L-z) = R(z)$, in turn implying that $\tilde{\beta}_F(2L-z) = \tilde{\beta}_F(z)$. Thus, Eq. (8) becomes:

$$\vec{\theta}_F = 2\int_0^L R(z)\vec{\beta}_F(z) dz. \tag{9}$$

So far, no assumption about the birefringence $\vec{\beta}_0(z)$ has been made. It may be linear, or elliptical, and its dependence on z could be arbitrary as well. In one embodiment, the birefringence is assumed to be linear, implying that the vector $\vec{\beta}_0(z)$ lies on the equator of the Poincare sphere and so does its frequency derivative $\vec{\beta}_w(z)$. In addition, to simplify the analysis, a circular and constant Faraday birefringence, $\vec{\beta}_F(z) = \vec{\beta}_F \hat{s}_3$ is assumed.

It is possible to show that the solution of equation (7) can be expressed in the form of a Dyson series. Posing $R(0,z) = R(z)$, we have:

$$R(z_0+z) = \tag{10}$$
$$I + \sum_{m=1}^{\infty}(-1)^m \int_{D_m} d^m\zeta [\vec{\beta}_0(\zeta_1) \times][\vec{\beta}_0(\zeta_2) \times]\ldots[\vec{\beta}_0(\zeta_m) \times],$$

where a z-ordered domain $D_m = \{z_0 \leq z_1 \leq z, z_0 \leq z_2 \leq z_1, \ldots z_0 \leq z_m \leq z_{m-1}\}$ is defined. This form of $R(z_0,z)$ may be verified by using the expansion in equation (6). In order to derive an expression for the average of $R(z_0,z)\vec{\beta}_F$, $[-\vec{\beta}_0(z')\times][-\vec{\beta}_0(z'')\times]\vec{\beta}_F = -[\vec{\beta}_0(z') \cdot \vec{\beta}_0(z'')]\vec{\beta}_F$ is first used iteratively. It is then assumed that $\vec{\beta}_0(z)$ is isotropically distributed on the equator of the Stokes space. The following is therefore obtained:

$$\langle R(z_0,z)\vec{\beta}_F\rangle = \{1 - \int_{D_2} d^2z \langle [\vec{\beta}_0(z_1) \cdot \vec{\beta}_0(z_2)]\rangle + \int_{D_4} d^4z$$
$$\langle [\vec{\beta}_0(z_1) \cdot \vec{\beta}_0(z_2)][\vec{\beta}_0(z_3) \cdot \vec{\beta}_0(z_4)]\rangle \ldots\}\vec{\beta}_F, \tag{11}$$

where brackets denote ensemble averaging. A further assumption that can be made on the birefringence is that, in the analytical calculations, a model in which the modulus of the birefringence is fixed whereas the orientation is a random process. Let the correlation function of $\vec{\beta}_0(z)$ be:

$$\langle \vec{\beta}_0(z) \cdot \vec{\beta}_0(z')\rangle = \beta_0^2 C(z-z') \tag{12}$$

with $C(0) = 1$ and $C(x) = C(-x)$. Within this model, the averages of products in expansion (11) factorize into products of averages and Eq. (12) can be simplified to:

$$\langle R(z_0,z)\vec{\beta}_F\rangle = R(z-z_0)\vec{\beta}_F \tag{13}$$

with $$R(z-z_0) = \begin{cases} 1 - \beta_0^2 \int_{D_2} d^2 z C(z_1-z_2) + \\ \beta_0^4 \int_{D_4} d^4 z C(z_1-z_2)C(z_3-z_4) + \ldots \end{cases}, \tag{14}$$

equivalent to the following integro-differential equation, $$\frac{dR(z)}{dz} = -\beta_0^2 \int_0^z dz' C(z-z')R(z'), \tag{15}$$

where, without loss of generality, we used $z_0 = 0$. Laplace transforming both sides of the equation and using the convolution theorem, the following is obtained:

$$s\tilde{R}(s) - R(0) = -\beta_0^2 \tilde{C}(s)\tilde{R}(s), \tag{16}$$

where tilde denotes the Laplace transform and s is the variable of Laplace. This equation, solved for $\tilde{R}(s)$ with initial condition $R(0) = 1$, gives $$\tilde{R}(s) = \frac{1}{s + \beta_0^2 \tilde{C}(s)}, \tag{17}$$

which once inverse transformed gives the solution of (15).

The statistics of $\vec{\theta}_F$ can be elaborated, evaluating its average square value, $\alpha(z) = \langle \theta_F^2(z)\rangle$. It can be shown that $$a(z) = 8\beta_F^2 \int_0^z dz' \int_0^{z'} dz'' R(z'-z'') \tag{18}$$
$$= 8\beta_F^2 \int_0^z dz'(z-z')R(z').$$

Performing the Laplace transform, the following is obtained:

$$\tilde{a}(s) = \frac{8\beta_F^2}{s^2[s + \beta_0^2 \tilde{C}(s)]}, \tag{19}$$

For large z, the asymptotic behavior is determined by the limit for $s \to 0$, that is $$\tilde{a}(s) \sim \frac{8\beta_F^2}{s^2 \beta_0^2 L_0}, s \to 0, \tag{20}$$

implying that, at z=L $$\langle \theta_F^2 \rangle \sim \frac{8\beta_F^2 L}{\beta_0^2 L_0}, L \to \infty, \tag{21}$$

where the distance $L_0 = \tilde{C}(0) = \int_0^\infty C(z)dz$ is an effective correlation length of the fiber birefringence. Based on the Central Limit Theorem, the result of Eq. (21) is independent on the model assumed for the birefringence, as long as this is represented by a stationary process.

Assume now an oscillating double-exponential form for the correlation function of the birefringence $$C(z - z') = \cos\left[\frac{4\pi}{L_t}(z - z')\right] \exp\left(-\frac{|z - z'|}{L_F}\right). \quad (22)$$

This is the case in which a constant spin is applied to the fiber during the drawing process to reduce the fiber PMD. This correlation function is consistent with a rotation of $\vec{\beta}_0$ with the constant spatial rate $2\pi/L_t$ to which is superimposed a random walk of the vector orientation. For this choice of the birefringence correlation, $\tilde{R}(s)$ can be evaluated analytically, $$\tilde{R}(s) = \frac{(s + 1/L_F)^2 + (4\pi/L_t)^2}{s[(s + 1/L_F)^2 + (4\pi/L_t)^2 + \beta_0^2] + \beta_0^2/L_F}, \quad (23)$$

and so does, in consequence, the average square angle. The asymptotic expression (21) of $\langle\theta_F^2\rangle$ can be specialized to the case under scrutiny by using (22) in the algebraic evaluation of $L_0$, with the result:

$$\langle\theta_F^2\rangle = \frac{8\beta_F^2 L}{\beta_0^2 L_F}\left[1 + \left(\frac{4\pi L_F}{L_t}\right)^2\right]. \quad (24)$$

An estimate of the lengths over which the asymptotic regime is reached is $L > 1/(\text{Re}a/(\kappa))$ where $\kappa$ is the pole of $\tilde{R}(s)$ with the smallest real part. In the limit of $L_t \ll L_B, L_F$, inspection of the denominator of $\tilde{R}(s)$ gives $$\frac{1}{\kappa} \sim \frac{L_F}{\beta_0^2}\left(\frac{4\pi}{L_t}\right)^2 = \frac{4L_B^2 L_F}{L_t^2}, \quad (25)$$

where $L_B = 2\pi/\beta_0$. For example, suppose $L_B = 19$ m and $L_F = 20$ m. If $L_t = 1$ m, the distance over which the asymptotic behavior is reached is $1/\kappa \sim 29$ km, whereas it is $1/\kappa \sim 1$ km if $L_t = 5$ m, and shorter for longer $L_t$. Another limit is $L_t \to 0$ and arbitrary $L$. In this case, $\tilde{R}(s) \cong 1/s$ implying that, at $z = L$, $\langle\theta_F^2\rangle \cong \beta_F^2(2L)^2$ is obtained. This result means that in the limit of very fast spinning rate, the random linear birefringence becomes ineffective and the fiber behaves like an ideal isotropic fiber of length 2L (the round-trip length) having only the circular birefringence induced by the Faraday effect.

Figure 3:
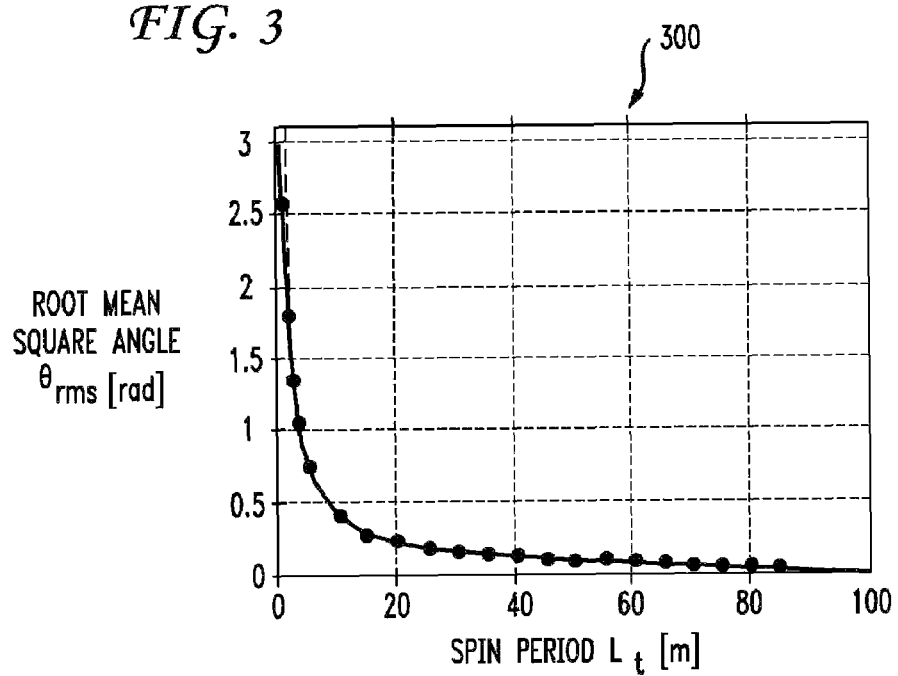
FIG. 3 is a graph of analytical results compared with computer simulations performed by using a random modulus model for the birefringence of a fiber in accordance with an embodiment of the present invention.

FIG. 3 shows a graph 300 of the analytical results compared with computer simulations performed by using the random modulus model for the birefringence. The net dependence of the magnitude of the rotation $\theta_F$ on the spin period is shown in FIG. 3, where the root mean square of the rotation, $\theta_{rms} = \sqrt{\langle\theta_F^2\rangle}$, is plotted versus the spin period, $L_t$. The solid line refers to the analytical result of Eq. (23), while the dashed line is the asymptotic expression of Eq. (24) and the circles are the results of a Monte Carlo simulation.

Simulations where made for $L_B = 19$ m, $L_F = 20$ m, and for the fiber length of $L = 25$ km. Both theory and simulation predict, for typical values of the spin period in the range of tens of meters, values of $\theta_{rms}$ which are on the same order of magnitude as the experimental measurements. As expected, as $L = 25$ km is smaller than $1/\kappa$ for $L_t = 1$ m, only the first point is outside the range of validity of the asymptotic expression.

Thus, a method and apparatus for determining the autocorrelation length of the fiber birefringence is disclosed. In the asymptotic regime, the expression for the mean square DGD, $\langle\tau^2\rangle = 2\beta_0^2 L_F L/\omega^2$, where $\omega/2\pi$ is the optical frequency, can be used to remove the dependence of Eq. (24) on the beat length as follows:

$$\langle\tau^2\rangle\langle\theta_F^2\rangle = \frac{16\beta_F^2 L^2}{\omega^2}\left[1 + \left(\frac{4\pi L_F}{L_t}\right)^2\right]. \quad (26)$$

This way, for given fiber length and spin period, and for measured values of PMD and rotation angle, Eq. (26) can be solved for the autocorrelation length of the fiber birefringence, $L_F$.

Specifically, Eq. (26) can be used to obtain the following formula:

$$\frac{L_F}{L_t} = \frac{1}{4\pi}\left[\frac{\omega^2\langle\tau^2\rangle\langle\theta_F^2\rangle}{16\beta_F^2 L^2} - 1\right]^{1/2}. \quad (27)$$

Figure 4:
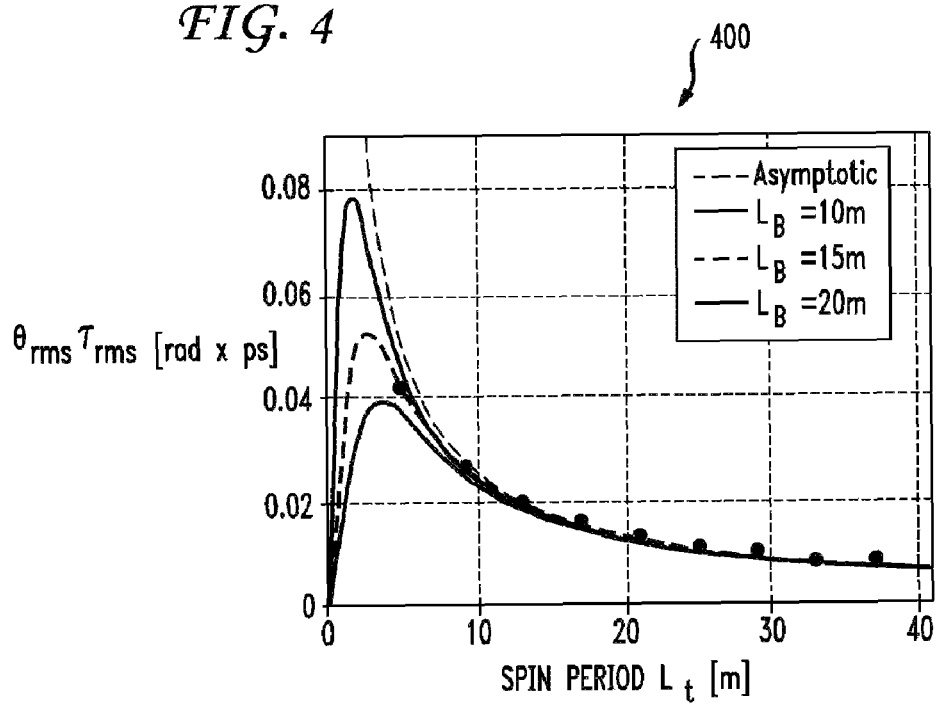
FIG. 4 is a graph of the product $\tau_{rms}\theta_{rms} = \sqrt{\langle \tau^2 \rangle \langle \theta_F^2 \rangle}$ for several values of the beat length $L_B$ for fiber length L=5 km and for $L_F$=20 m in accordance with an embodiment of the present invention.

FIG. 4 shows a graph 400 of the product $\tau_{rms}\theta_{rms} = \sqrt{\langle\tau^2\rangle\langle\theta_F^2\rangle}$ for several values of the beat length $L_B$ for fiber length $L = 5$ km and for $L_F = 20$ m. Specifically, in FIG. 4, the product $\tau_{rms}\theta_{rms} = \sqrt{\langle\tau^2\rangle\langle\theta_F^2\rangle}$ is plotted versus the spin period by the solid lines for the values of the beat length, while the asymptotic expression of Eq. (26) is plotted by a dashed line. Dots refer to a Monte Carlo simulation made for $L_B = 15$ m. The plot confirms the independence of the product $\tau_{rms}\theta_{rms}$ on the beat length, already for small values of the spin period.

Periodically Spun Fibers

PMD of fibers can be further reduced by optimizing the spin pattern, which can be done by making the angular velocity of the spinner time dependent. The rotation of the spinner can be described by the periodic function $A(z)$, that is assumed here to be periodic. The period Z gives the length of the preform drawn by the spinner to repeat its angular position and velocity. Recall the asymptotic expression for the Faraday rotation angle, given by Eq. (21) above:

$$\langle\theta_F^2\rangle \approx \frac{8\beta_F^2 L}{\beta_0^2 \tilde{C}_0}, \quad (28)$$

with $$\tilde{C}_0 = Z^{-1}\left[1 - \exp\left(-\frac{Z}{L_F}\right)\right]^{-1} \times \int_0^z \int_0^z e^{-\frac{u}{L_F}} \cos\left\{2\begin{bmatrix}A(z) - \\ A(z-u)\end{bmatrix}\right\} du\, dz.$$

The asymptotic expression for the mean square DGD can be written as follows:

$$\langle\tau^2\rangle = \frac{2\beta_0^2 L_F L}{\omega^2} \frac{1}{L_F} \frac{\tilde{C}_0^2 + \tilde{S}_0^2}{\tilde{C}_0} \quad (29)$$

with $$\tilde{S}_0 = Z^{-1}\left[1 - \exp\left(-\frac{Z}{L_F}\right)\right]^{-1} \times \int_0^z \int_0^z e^{-\frac{u}{L_F}} \sin\left\{2\begin{bmatrix}A(z) - \\ A(z-u)\end{bmatrix}\right\} du\, dz.$$

As described above, multiplying the two equations, an expression independent of the beat length is obtained:

$$\langle\theta_F^2\rangle\langle\tau^2\rangle = \frac{16\beta_F^2 L^2}{\omega^2}\left(1+\frac{\tilde{S}_0^2}{\tilde{C}_0^2}\right) \qquad (30)$$

Inversion of Eq. (30) in favor of $L_F$ is not straightforward. In general, for a given spin pattern, Eq. (30) can be plotted versus the autocorrelation length of the fiber birefringence. Thus, the value of $L_F$ for which the plot meets the experimentally measured value of $\langle\theta_F^2\rangle\langle\tau^2\rangle$ represents the wanted estimate of the correlation length.

Below is a numerical example. Consider the following spin function:

$$A(z) = A_0\left[\sin\left(\frac{2\pi}{Z}z\right) + 2\sin\left(\frac{4\pi}{Z}z\right)\right] \qquad (31)$$

Figure 5:
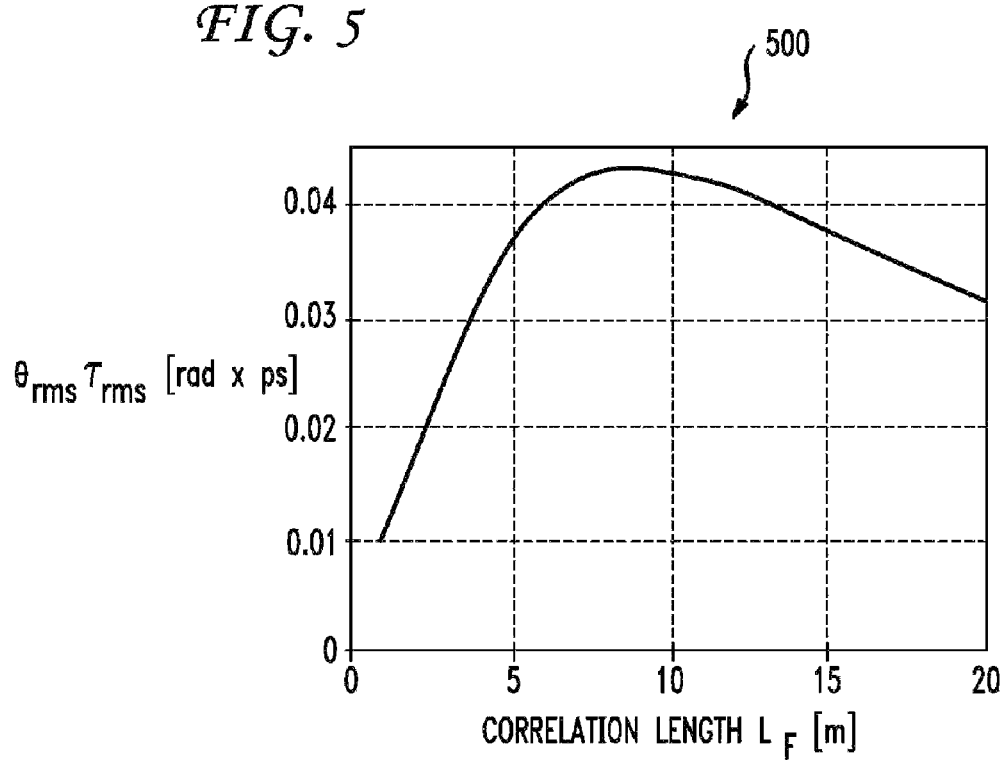
FIG. 5 is a graph of the product $\tau_{rms}\theta_{rms}$ versus the autocorrelation length $L_F$ of a fiber in accordance with an embodiment of the present invention.

The spin amplitude can be $A_0=1.2$ rad and the spin period $Z=4$ m. For these parameter values, Eq. (30) is plotted versus $L_F$ in FIG. 5. Specifically, FIG. 5 shows a graph 500 of the product $\tau_{rms}\theta_{rms}$ versus the autocorrelation length $L_F$. Corresponding to the exemplary values (L, $\tau_{rms}$, $\theta_{rms}$)≅(25 km; 0.2 ps; 0.2 rad), the product $\tau_{rms}\theta_{rms}$≅0.04 is evaluated, which gives the two estimates $L_F$≅6 m or $L_F$≅13 m.

It should be pointed out that, for some classes of spin functions, the integral in the definition of $\tilde{S}_0$ vanishes, thus the asymptotic value of $(\theta_F^2)(\tau^2)$ becomes independent of the birefringence autocorrelation length. Nonetheless, this property, while invalidating the use of angle measurements for estimating $L_F$, allows the measuring of the birefringence induced by the geomagnetic field $\beta_F$. For $\tilde{S}_0$0 this can be done by solving Eq. (30) in favor of $\beta_F$, which gives $\beta_F=\omega\theta_{rms}\tau_{rms}/4L$. B2

Figure 6:
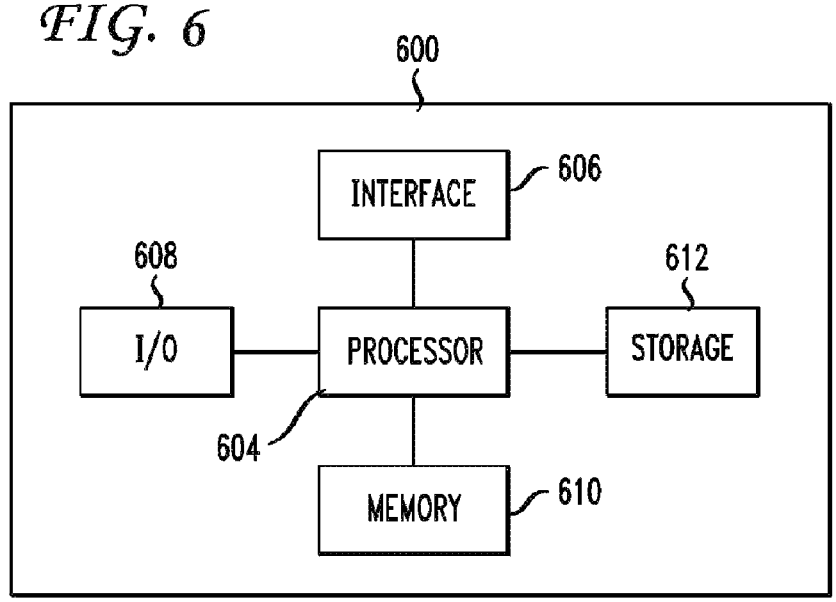
FIG. 6 is a high level block diagram of a computer system which may be used in an embodiment of the invention.

FIG. 6 shows a high level block diagram of a computer that may be used to perform the calculations described above. Computer 600 contains a processor 604 which controls the overall operation of the computer by executing computer program instructions which define such operation. The computer program instructions may be stored in a storage device 612 (e.g., magnetic disk, database) and loaded into memory 610 when execution of the computer program instructions is desired. Thus, the computer operation will be defined by computer program instructions stored in memory 610 and/or storage 612 and the computer will be controlled by processor 604 executing the computer program instructions. Computer 600 also includes one or more input network interfaces 606 for communicating with other devices via a network (e.g., the Internet). Computer 600 also includes one or more output network interfaces 606 for communicating with other devices. Computer 600 also includes input/output 608 which represents devices which allow for user interaction with the computer 600 (e.g., display, keyboard, mouse, speakers, buttons, etc.). One skilled in the art will recognize that an implementation of an actual computer will contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method of determining characteristics of a fiber comprising:
    measuring, at a computer, polarization mode dispersion (PMD) of an optical fiber;
    measuring a rotation angle; and
    determining birefringence autocorrelation length from the measuring of the PMD and the rotation angle, wherein the birefringence autocorrelation length, $L_F$, is determined by the following equation:

$$\langle\tau^2\rangle\langle\theta_F^2\rangle = \frac{16\beta_F^2 L^2}{\omega^2}\left[1+\left(\frac{4\pi L_F}{L_t}\right)^2\right],$$

where $\tau$ represents a differential group delay, $\theta_F$ represents a rotation angle, $\beta_F$ represents a fiber birefringence, L represents a fiber length, and $\omega$ represents a frequency and $L_t$ represents a spin period.

2. The method of claim 1 wherein the birefringence autocorrelation length is determined in a non-destructive manner.

3. The method of claim 1 further comprising determining a beat length.

4. The method of claim 1 further comprising determining a polarization birefringence.

5. An article of manufacture including a non-transitory computer-readable medium having instructions stored thereon that, if executed by a computing device, cause the computing device to perform operations comprising:
    measuring polarization mode dispersion (PMD) of an optical fiber;
    measuring a rotation angle; and
    determining birefringence autocorrelation length from the measuring of the PMD and the rotation angle, wherein the birefringence autocorrelation length, $L_F$, is determined by the following equation:

$$\langle\tau^2\rangle\langle\theta_F^2\rangle = \frac{16\beta_F^2 L^2}{\omega^2}\left[1+\left(\frac{4\pi L_F}{L_t}\right)^2\right],$$

where $\tau$ represents a differential group delay, $\theta_F$ represents a rotation angle, $\beta_F$ represents a fiber birefringence, L represents a fiber length, and $\omega$ represents a frequency and $L_t$ represents a spin period.

6. The article of manufacture of claim 5 wherein the birefringence autocorrelation length is determined in a non-destructive manner.

7. The article of manufacture of claim 5 wherein the operations further comprise determining a beat length.

8. The article of manufacture of claim 5 wherein the operations further comprise determining a polarization birefringence.

* * * * *